United States Patent
Liu et al.

(10) Patent No.: US 7,946,176 B2
(45) Date of Patent: May 24, 2011

(54) METHODS AND APPARATUS FOR EXTRACTING FIRST ARRIVAL WAVE PACKETS IN A STRUCTURAL HEALTH MONITORING SYSTEM

(75) Inventors: Bao Liu, Cupertino, CA (US); Shawn J Beard, Livermore, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 575 days.

(21) Appl. No.: 12/049,061

(22) Filed: Mar. 14, 2008

(65) Prior Publication Data
US 2008/0253229 A1    Oct. 16, 2008

Related U.S. Application Data

(60) Provisional application No. 60/912,112, filed on Apr. 16, 2007.

(51) Int. Cl.
*G01N 29/38* (2006.01)
*G01N 29/40* (2006.01)

(52) U.S. Cl. .................. 73/597; 73/609; 702/39

(58) Field of Classification Search .......... 73/597, 73/865.9, 609–612; 702/34–36, 39
See application file for complete search history.

(56) References Cited

U.S. PATENT DOCUMENTS

| | | | |
|---|---|---|---|
| 5,163,013 A * | 11/1992 | Herzer et al. | 702/171 |
| 6,006,163 A * | 12/1999 | Lichtenwalner et al. | 702/36 |
| 6,370,964 B1 * | 4/2002 | Chang et al. | 73/862.046 |
| 2003/0009300 A1 * | 1/2003 | Giurgiutiu | 702/35 |
| 2005/0075846 A1 * | 4/2005 | Kim | 703/1 |
| 2005/0228597 A1 * | 10/2005 | Giurgiutiu et al. | 702/35 |
| 2006/0106550 A1 * | 5/2006 | Morin et al. | 702/34 |
| 2006/0106551 A1 * | 5/2006 | Morin et al. | 702/35 |
| 2007/0055160 A1 * | 3/2007 | Ng | 600/447 |
| 2007/0240515 A1 * | 10/2007 | Kessler et al. | 73/597 |
| 2008/0253231 A1 * | 10/2008 | Yu et al. | 367/140 |
| 2008/0255771 A1 * | 10/2008 | Beard | 702/34 |
| 2008/0255774 A1 * | 10/2008 | Liu et al. | 702/34 |
| 2008/0255776 A1 * | 10/2008 | Beard | 702/35 |
| 2008/0255777 A1 * | 10/2008 | Beard et al. | 702/35 |
| 2008/0255778 A1 * | 10/2008 | Liu et al. | 702/35 |
| 2008/0255803 A1 * | 10/2008 | Beard et al. | 702/181 |

\* cited by examiner

*Primary Examiner* — Hezron Williams
*Assistant Examiner* — Rose M Miller
(74) *Attorney, Agent, or Firm* — Innovation Counsel LLP

(57) ABSTRACT

Methods and apparatus for extracting the first arrival wave packet of an acoustic signal in a structural health monitoring (SHM) system include receiving an acoustic signal transmitted between two transducers thereof. Electromagnetic crosstalk is removed from the signal. Signal amplitude threshold values used for picking out the first arrival wave packet are chosen based on signal characteristics or chosen adaptively as the value that leads to the minimum variance of the group velocity estimates of all the actuation-sensing transducer pairs. The group velocity is estimated as the known actuator-sensor distance divided by the propagation time of the first wave packet of which the envelope exceeds a candidate threshold value. The first arrival wave packet is determined as the signal segment where the signal envelope first exceeds the chosen amplitude threshold and the segment length exceeds a specified threshold of time width.

6 Claims, 7 Drawing Sheets

Threshold = 20

Threshold = 100

Threshold = 300

METHODS AND APPARATUS FOR EXTRACTING FIRST ARRIVAL WAVE PACKETS IN A STRUCTURAL HEALTH MONITORING SYSTEM

This application claims the benefit of U.S. Provisional Patent Application No. 60/912,112, entitled "STRUCTURAL HEALTH MONITORING SYSTEM AND METHODS FOR USE," filed Apr. 16, 2007, the entire disclosure of which is incorporated herein by reference.

BRIEF DESCRIPTION OF THE INVENTION

This invention relates generally to structural health monitoring (SHM) systems and Lamb wave signal analysis. More specifically, this invention relates to the extraction of the first arrival wave packet at a transducer of the system from a recorded waveform.

BACKGROUND OF THE INVENTION

Many structures are comprised of plate-like features. In such structures, elastic waves may include Lamb waves as at least one form of elastic wave propagation therein. In addition, the structural material may be anisotropic in terms of its elastic properties, which is quite typical of structural composites. The result may be strong dispersion characteristics, causing a pulsed elastic waveform transmitted from an actuator to change shape and length significantly over the distance of the propagation path. The pulse may break up into several different modes, each of which may have different propagation velocities, depending on the wavelength relative to plate thickness, direction of propagation, and other factors. As a result, the received signal waveform may be very different and more complex as compared to the original pulse launched at the actuator. Specifically, the transmitted pulse may then include the first arrivals of different modes and scatters of these modes. However, because of the complexity of structures and the dispersion, these signal components may overlap and interfere with each other, making it very difficult to understand the composition of the signal received at a sensor of the SHM system.

The "first arrival" signal is the elastic wave component that propagates from an actuator to the sensor, and may be defined as the signal arriving at a time at which the signal exceeds a particular amplitude threshold. Since the property of this component is relatively easy to understand, it has been considered the most useful component for Lamb-wave-based structural health monitoring (SHM). The accuracy of first arrival detection is thus very important. The first arrival signal, however, may include a direct path propagation between the actuator and the sensor transducers plus a scattered, or reflected, wave from a damage in the neighborhood of the direct path. While the direct path propagating wave may not detect the damage, the scattered wave, when detected at the sensor transducer, will coherently interfere with the direct path wave, producing a more complicated received signal, which nevertheless, when properly treated, as described below, is useful in detection of damage.

Accurate detection of first arrival, however, may not be an easy task. Perhaps the most commonly used method now may be visual selection by inspection of the waveform data. However, this method is practically infeasible for the monitoring of relatively large structures, where thousands of signal paths may be implemented. Thus, automation of the process would be highly advantageous. The most straightforward automatic way is directly picking up the first signal wave packet that has relatively large components. However, this approach may fail in many situations because the electromagnetic interference (EMI) cross-talk between the actuation and sensor channels may easily exceed the magnitude of the electromechanically detected elastic wave, so that signal thresholding is not useful until cross-talk can be properly treated in an appropriate manner. The noisy shape of the elastic wave may increase the difficulty of automatically detecting the starting and ending points of the first signal arrival. Therefore, it is desirable to have methods and systems for the automatic removal of the EMI cross-talk, as well as the detecting of the first arrival signals.

SUMMARY OF THE INVENTION

In accordance with the present disclosure, SHM methods and systems are described for removing the EMI cross-talk and for detecting the first arrival elastic waves.

A method for removing cross-talk from a signal waveform transmitted between a first and a second transducer includes specifying an upper bound for a group velocity of a signal transmitted on a selected path between the first and second transducer. A lower bound of a time of transmission along the selected path results and is computed by dividing the distance of the selected path by the specified upper bound of the group velocity. A gate time equal to the sum of the lower bound of the transmission time and a trigger time corresponding to the excitation of the signal at the first transducer is computed. Only data in a signal waveform corresponding to times greater than the gate time are retained.

According to a first embodiment of the disclosure, a method for extracting the first arrival time of a wave packet in a health monitoring system includes receiving detected excitation signals from a selected path between two transducers in a transducer array attached to a structure for health monitoring and removing electromagnetic cross-talk from the excitation signals. Threshold values for signal amplitude and width of a time window are specified. An envelope of the received excitation signal in the time window is computed and the time locations of all local maxima in the envelope of the signal within the time window are determined. The first maximum in the time window is selected and the time width of the first local maximum with signal amplitude greater than the amplitude threshold is measured. The first arrival time is determined as the time at which the envelope first exceeds the amplitude threshold within the specified time window. If the envelope does not exceed the amplitude threshold in the specified time window, it is deemed that no first arrival was detected.

According to a second embodiment of the disclosure, a method for extracting the first arrival time of a wave packet in a health monitoring system includes receiving a detected excitation signal corresponding to each of one or more selected paths between a first and a second transducer in an array comprised of a plurality of transducers attached to a structure for health monitoring. Electromagnetic cross-talk is removed from each of the received signals. An envelope of each of the excitation signals applied at each of the first of the one or more transducers and the corresponding signal received at the second of the one or more transducers is computed. A set of candidate amplitude thresholds is defined for the received envelope signals. A first candidate amplitude threshold is selected from the set of candidate amplitude thresholds. The propagation time of the first arrival wave packet is computed as the time from the instant of the maximum of the excitation signal envelope to the instant of the first local maximum of the received signal envelope that exceeds the first candidate amplitude threshold. The group velocity for each path is computed, wherein the group velocity is determined by the propagation time of the first arrival wave packet and the distance between the first and second transducer of each path. A "cost value" corresponding to the candidate amplitude threshold is computed, wherein the cost value is the variance of all group velocities calculated for each of the paths determined according to the selected candidate amplitude threshold. The steps of selecting, setting, computing the group velocity, and computing the cost value is repeated for all candidate amplitude thresholds in the set of candidate amplitude thresholds. The optimal amplitude threshold is selected, wherein the optimal amplitude threshold is the candidate amplitude threshold with the lowest cost value of all the cost values computed for all candidate amplitude thresholds. The first arrival time is chosen for each path based on the selected threshold.

These and other features and advantages of the present invention will be more readily apparent from the detailed description of the preferred embodiments set forth below taken in conjunction with the accompanying drawings, wherein the same or like elements are referred to by the same or like reference numerals throughout.

DETAILED DESCRIPTION

EMI cross-talk is a common and unavoidable problem in high frequency, high voltage electronic sensor systems, particularly if the sensors also function as actuators. Thus, the transducer cables, and connectors may also be efficient antennas for detection as well as generation of electromagnetic radiation of the signal. When the structures involved are composites, such as graphite-epoxy laminates, or are otherwise poor conductors at frequencies commonly used in Lamb wave excitation, direct cross-talk EMI may become especially troublesome. Since the cross-talk signal may have an amplitude greater than the corresponding elastic wave signal and the amplitude of the elastic wave signal may itself also vary in significant and complex ways, removing cross-talk therefore becomes an indispensable first step in processing the elastic wave signals usefully.

Figure 1:
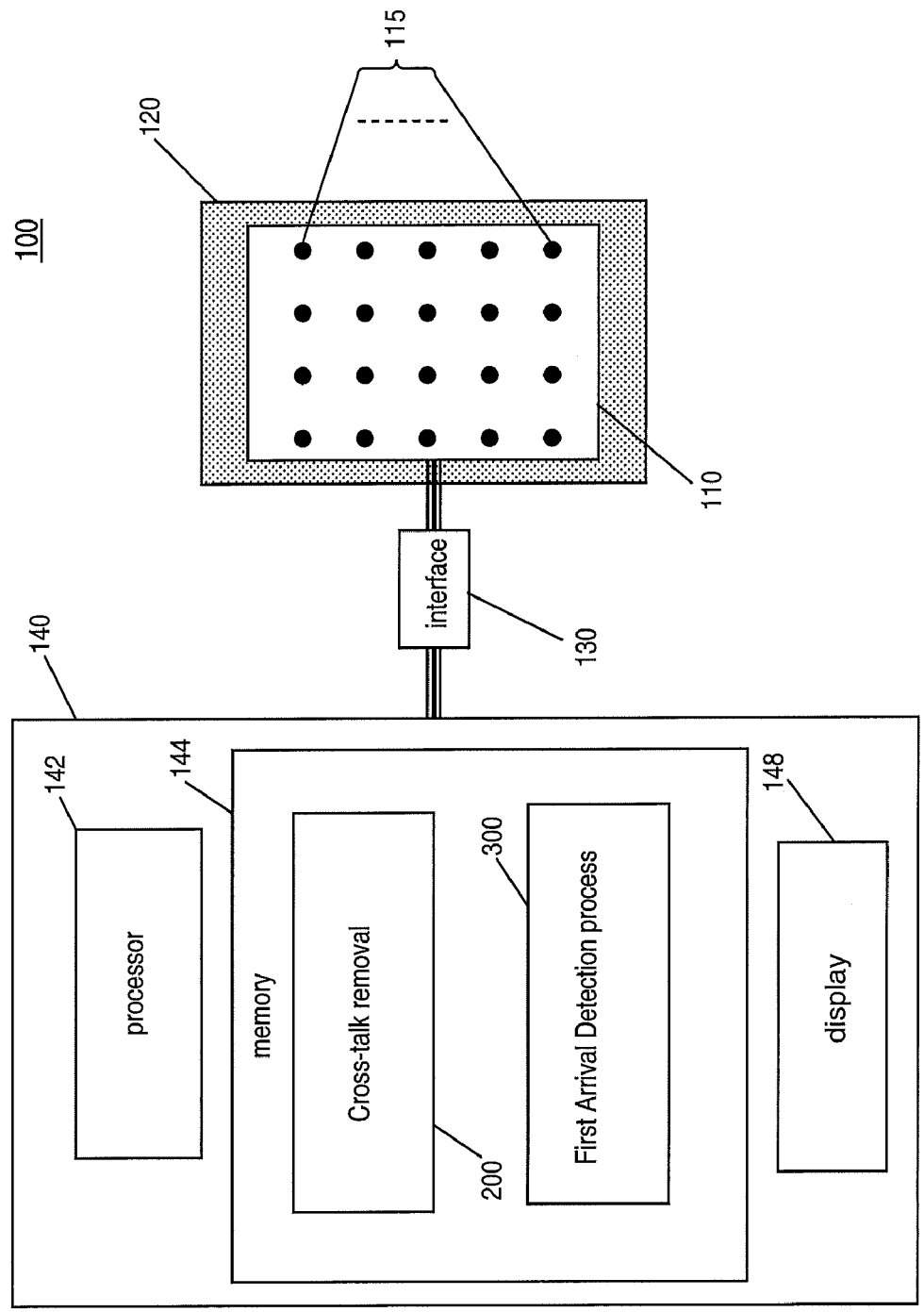
FIG. 1 illustrates a system for extracting the first arrival wave packet in a structural health monitoring system according to an embodiment of the present disclosure.

FIG. 1 illustrates one embodiment of a system 100 for extracting the first arrival wave packet in a structural health monitoring (SHM) system. The system 100 includes an array 110 of transducers 115 attached to a structure 120 to be monitored for damage detection. The transducers may comprise, for example, piezoelectric transducers, e.g., lead-zirconium-titanate (PZT) transducers capable of reversible operation, i.e., as both wave excitation actuators and sensors. Damage to the structure 120 may typically take the form of, for example, cracks that are internal to the structure or that open to the surface thereof, delaminations (especially in the case of laminated composites), or disbonds occurring at interfaces between structural components.

SHM system 100 may further include a connection, via an appropriate interface 130, to a computing system 140. Interface 130 provides for transmitting and routing excitation signals and control commands from computing system 140 to array 110 of transducers 115, and receiving signals detected by transducers 115 and providing the detected signals and associated routing information corresponding to each signal for input to computing system 140. Structural health monitoring may commonly be implemented where the excitation is an elastic wave, especially a Lamb wave, where the structures may include various plate-like components, and Lamb wave excitation and propagation is likely to occur. In such SHM systems, the transducers 115 may respond to an electrical input signal and excite elastic waves in the structure to which each transducer 115 of array 110 is bonded. Similarly, transducers 115 may be reversible in behavior, detecting elastic waves in the structure and converting the mechanical energy therein to an electrical signal. Such systems for excitation and detection of these and related elastic waves are well known in the art and will not be described in further detail in the following description.

In further accordance with the disclosure, computing system 140 comprises a processor for controlling all input/output signal processing through interface 130 to and from transducer array 110, and execution of one or more computing processes stored in a memory 144 for analysis of the excitation signal data obtained to improve the quality of signal detection and the accuracy of the associated SHM system. Processes stored in memory 144 may include a machine executable cross-talk removal method 200 for the gating, or removal, of electromagnetic interference cross-talk signals from the output signals obtained from the transducers 115 of the array. Memory 144 may further include machine executable methods 300 and/or 400 (not shown in FIG. 1) for the detection of first arrival signals. Methods 200, 300 and 400 are discussed in detail below.

Figure 2:
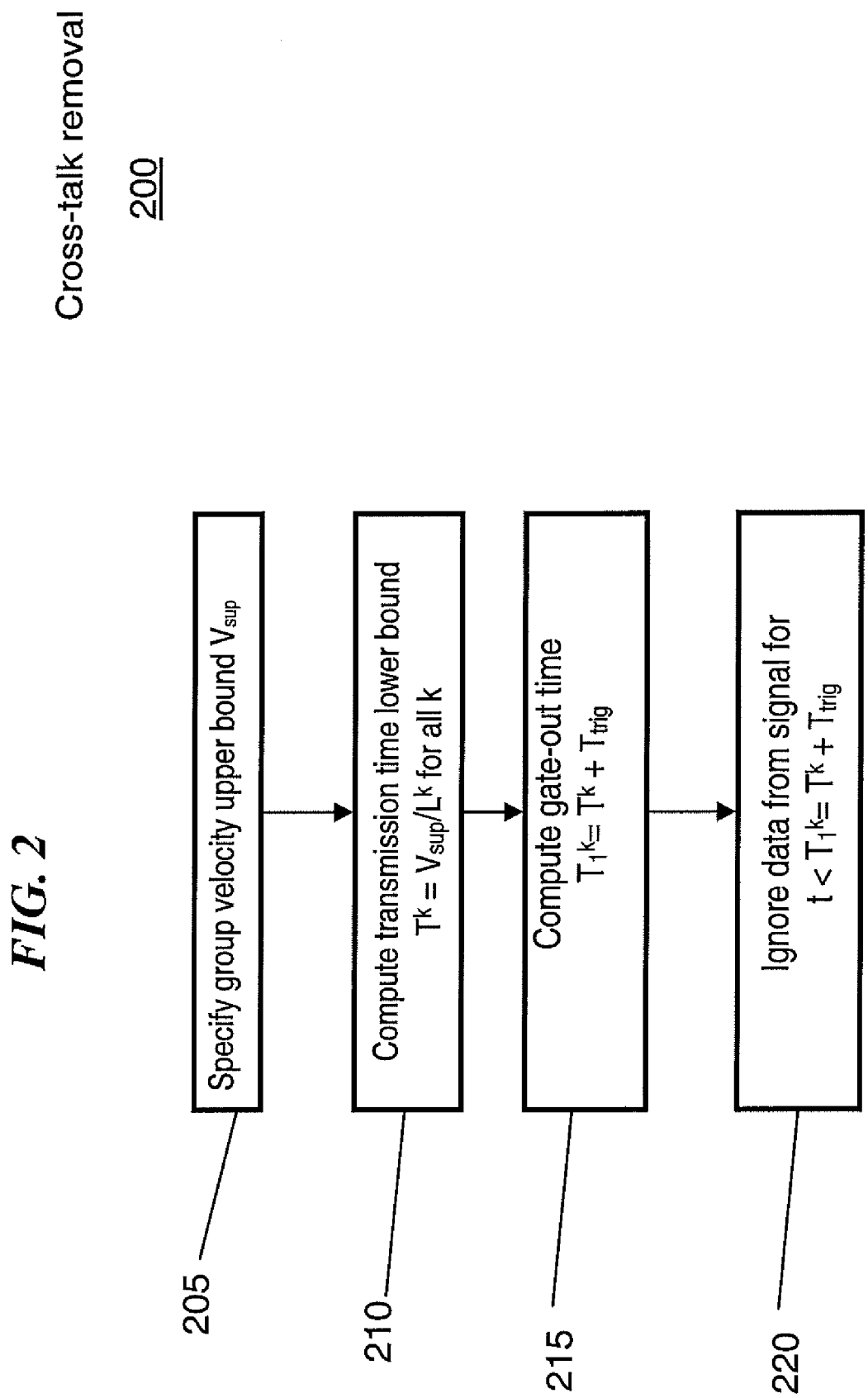
FIG. 2 is a process flow diagram of an embodiment of a method for removing cross-talk from a waveform in accordance with the present disclosure.

FIG. 2 is a process flow diagram of a cross-talk removal method 200 in accordance with an embodiment of the disclosure. In accordance with this method, a rough estimation of the upper bound of the elastic wave group velocity $V_{sup}$ may be supposed (block 205). Then, the lower bound of the transmission time is computed (block 210) as $T^k = L^k/V_{sup}$, where $L^k$ is the length of the kth path specified by two transducers, where the path specified by two transducers is simply the straight line path in the monitored structure between two transducers that is taken by an elastic wave in moving from one of the transducers to the other. The time $T_1^k = T^k + T_{trig}$ may then be chosen (block 215) as the maximum time for gating out the cross-talk component, where $T_{trig}$ is the time at which the actuator transducer was triggered so as to generate an elastic wave in the structure. Data in the signal corresponding to the kth path up to time $T_1^k$ may be ignored for further analysis (block 220). For example, this data may be replaced by null values, or alternatively, only the data for times greater than $T_1^k$ may be used in the further analysis.

$V_{sup}$ can be selected or estimated from a large range of values. It is thus a relatively easy matter to select $V_{sup}$ and only minimal knowledge about the structure is required. The choice of $V_{sup}$ may preferably be chosen to be somewhat less than the highest known actual group velocity in the structure. The resulting time interval $T_1^k$ may be used to define the minimum delay before a signal arriving at the receiving transducer (i.e., sensor) is measured so as to gate out the cross-talk arriving during the delay.

Since the speed of electromagnetic cross-talk is approximately five orders of magnitude greater than the group velocity of typical elastic waves, the time delay associated with the EMI interference may be assumed to be negligible, so that $V_{sup}$ may be chosen somewhat arbitrarily, provided the resulting $T^k$ is at least greater than the time length of the trigger pulse, i.e., as long as the cross-talk does not substantially overlap with the first arrival signal. It should be noted that, in the case where the cross-talk significantly overlaps with the first arrival, the damage detection will typically be unreliable since the amplitude of the cross-talk interference with the elastic wave signal detected may change the shape of the acquired signal considerably. Fortunately, in the health monitoring of large structures, where propagation delay is typically comfortably greater than the trigger pulse width, this is usually a rare occurrence.

After the process for eliminating EMI is performed using method 100, a second process, viz., the first arrival detection process, may proceed. Two advantageous embodiments for accomplishing this are described below.

Figure 3:
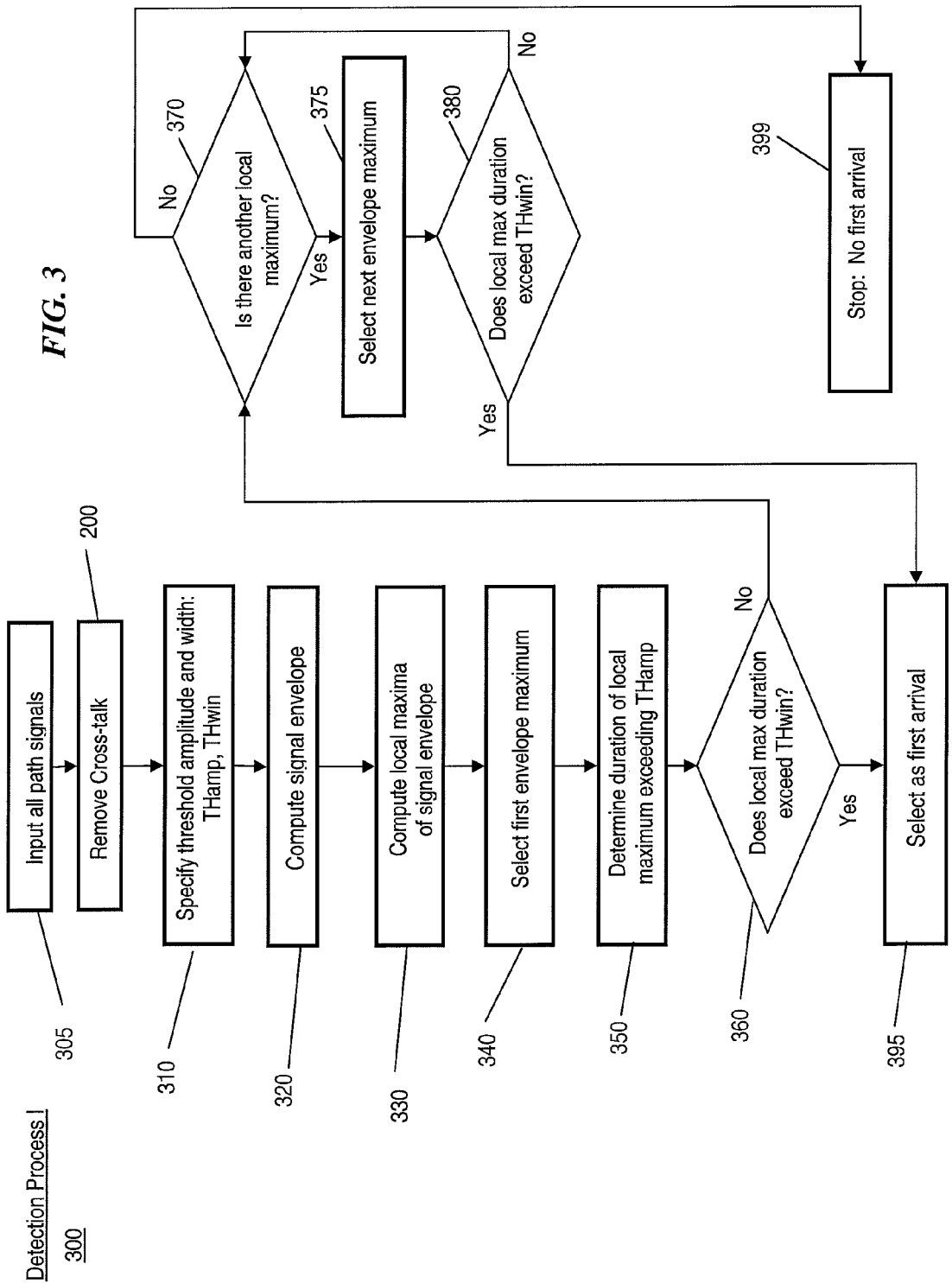
FIG. 3 is a process flow chart of an embodiment of a method for extracting the first arrival wave packet in a structural health monitoring system in accordance with the present disclosure.

FIG. 3 is a process flow diagram of one embodiment of a first arrival detection process 300 that uses the envelope of the signal to detect the first arrival based on the amplitude and width of a wave packet. Method 300 includes inputting (block 305) to computing system 140 all signals from all paths specified between transducers 115 of array 110. Method 200 described above for removal of cross-talk may be applied to all signals. A threshold specification (block 310), in which a threshold amplitude THamp and a threshold window of time width THwin for the first arrival signal, is selected. THwin may be selected on the basis of the time characteristics of the exciting signal applied to the transmitting sensor and the response of the transmitting sensor to that signal, which may be affected by mechanical resonance, electrical impedance, for reasons that will be made apparent below.

The window THwin begins at a time t1 that is at least greater than $T_1^k$ and that ends at t2=t1+THwin. The envelope of the signal detected at the receiving sensor may then be computed (block 320). Characterization of the envelope of the amplitude enables determination of the time at which the signal reaches or passes the amplitude threshold THamp, and the time width of the detected signal, as described in more detail below. Computing the signal envelope enables a determination of all local maxima (block 330) in a signal waveform following the time t1, where t1 is determined after the envelope is computed. The signal waveform may then be appropriately analyzed to select the first local maximum (block 340) in the window.

The envelope is analyzed about this local maximum to determine the time duration (block 350) of the local peak, defined as the time during which the envelope exceeds the amplitude threshold THamp. The time at which this occurs is t1, as defined above, and is required to be equal or greater than the time $T_1^k$ for eliminating EMI cross-talk. The time duration determination in block 350 then seeks the point in time at which the trailing edge of the signal envelope drops below THamp. If the time duration measurement (block 350) determines that the pulse width corresponding to the first maximum is broader than THwin (a "Yes" result in decision block 360) then the pulse is designated as a first arrival pulse, and the time of arrival is deemed to be t1. If the pulse is narrower than THwin (a "No" result in decision block 360), then that pulse is not considered as a first arrival pulse, but instead, may be noise, a weak signal or another artifact. In that case, the signal envelope is further examined to determine if there is another, later, local maximum (decision block 370).

If another local maximum in the envelope is found (a Yes result in decision block 370), this envelope local maximum is selected (block 375) and tested to determine if the envelope exceeds THamp for at least the duration of THwin (a Yes result in decision block 380), or is narrower than THwin (a No result in decision block 380), in a manner identical to the test performed in decision block 360. If the duration of the envelope does not exceed THamp for at least the duration of THwin, the signal envelope is evaluated in decision block 370, as before, to determine if there is another, later local maximum. If no further envelope peaks are detected (a No result in decision block 370) then it is determined that no first arrival packet was detected (block 399) in the signal envelope, and the detection process for the selected path is completed. If, however, a local maximum peak exceeds THamp for at least the duration of THwin (a Yes result in decision blocks 360 or 380), then that pulse segment is determined to be a first arrival pulse (block 395). In that case, the pulse arrival time t1, as described above, is the time at which that pulse segment first exceeds THamp. In no case may t1 be less than $T_1^k$. The detection process may then be repeated for another path in the array.

The decision methodology of the method 300 described above may be found most beneficial where the pulse signals detected are of "good quality" (i.e., those having only one or a few local maxima), that are clearly separable from both cross-talk and scattered pulse signals, and are of sufficient amplitude to set a reasonable threshold.

It may now be appreciated that the choice of THwin can be selected to substantially improve reliability of detection by requiring the first arrival pulse width to be greater than THwin. As indicated above, THwin bears a corresponding relation to the exciting pulse width at the transmitting sensor and the response of the sensor to the excitation. Thus, THwin is selected with the expectation that the received signal is greater than THamp for at least the duration of THwin. A narrower pulse may imply damage directly in the path of the transmitted wave, which attenuates the pulse, consequently reducing the pulse width that exceeds THamp, or there may be sensor damage, in which case the data obtained from that sensor (functioning as either a transmitter or detector) is considered unreliable. The size of THwin, together with THamp, thus determines whether a pulse with a local maximum is both wide and strong enough to qualify as a pulse representing a first arrival.

It may further be appreciated that varying THamp and THwin will result in different degrees of accuracy in determining the first arrival. Increasing THamp will reduce the likelihood of detecting any signal of marginal amplitude, whereas, lowering THamp may increase the detection of noise that may be mistaken for a possible first maximum. The beginning of THwin, i.e., t1, must be at least greater than $T_1^k$, the lower bound on transmission time for the kth path.

In some cases, the number of paths in the SHM system 110 may be relatively large, e.g., greater than 30, and the plurality of transducers (all of which may re-radiate elastic and electromagnetic signals as radiation) may result in increased noise and error in cross-talk removal. Furthermore, modal dispersion of waves excited in the structure may arrive at detecting transducers 115 as very complex signals. In such cases, a more robust method is therefore desirable.

Figure 4:
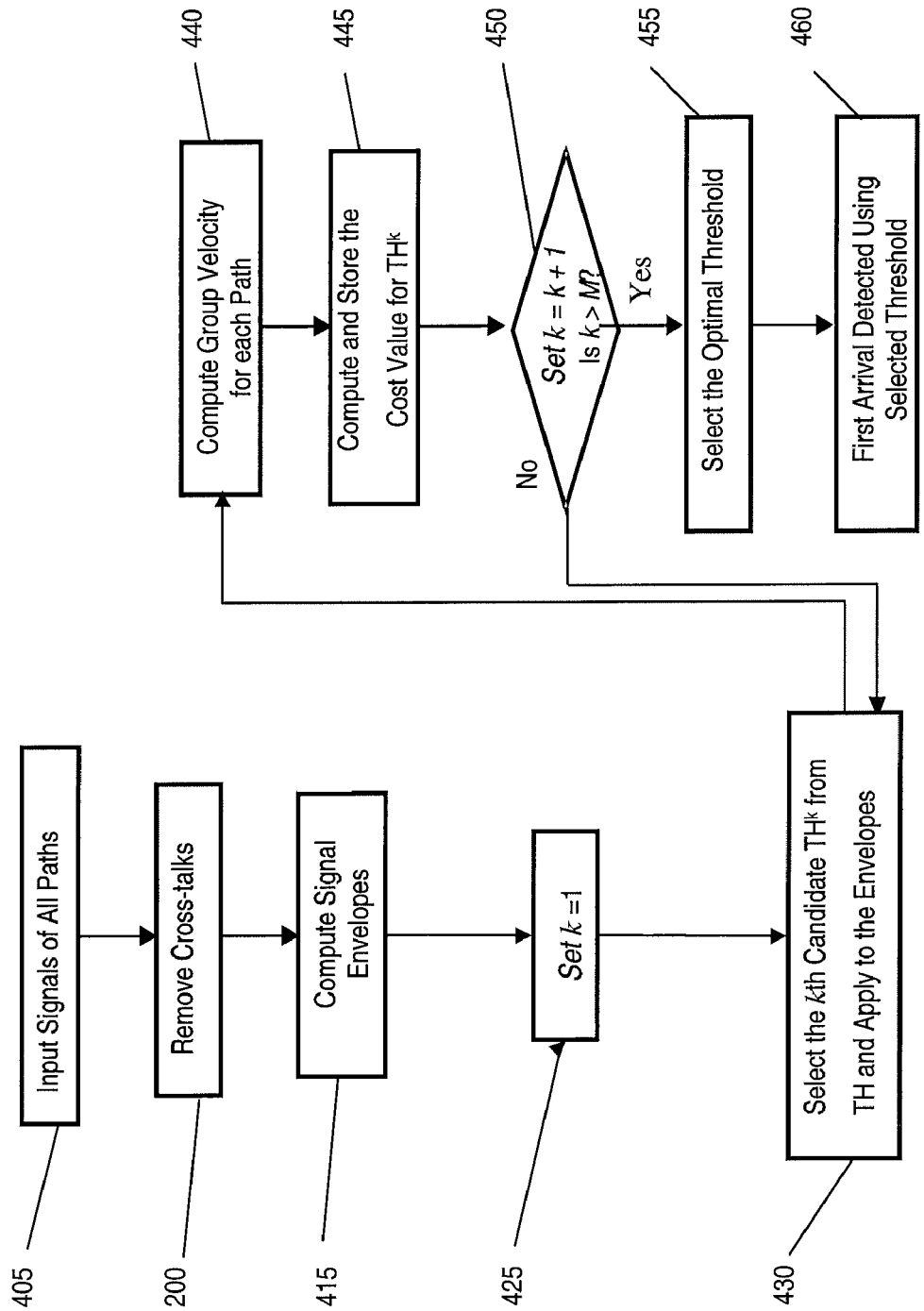
FIG. 4 is a process flow chart of another embodiment of a method for extracting the first arrival wave packet in a structural health monitoring system in accordance with the present disclosure.

Thus, in another embodiment of the disclosure, a second first arrival detection method 400 shown in FIG. 4 is based on the premise that the variation in estimated group velocity is minimized if the first arrivals of all the paths are detected as accurately as possible. A side benefit of this first arrival detection process is that it provides a way to estimate the signal group velocity in each path, which is potentially useful in damage analysis and detection.

Detection of the first arrival in method 400 may be considered as depending on the selection of a "best" threshold level. Automatic selection of the optimal threshold is a part of the first arrival determination process. While the process, in principle, may be iterative with efficient numerical implementation, method 400 contemplates a simplified procedure by selecting the optimal threshold from among a limited set of possible candidate threshold values. Candidate threshold values may be quickly generated, either arbitrarily, based on the data collected, or based on historical experience, for example, in selected increments, and may have little dependence on the specifics of the particular structure being monitored. Thus, in the second method 400, a detailed knowledge of the structure is not a prerequisite for the success of the method.

The threshold may be an absolute or a relative property. For example, in a defined absolute threshold, the minimum amplitude of the first arrival may be the defined threshold. In a defined relative threshold, the threshold value may be a defined ratio of the minimum first arrival amplitude divided by the maximum of the signal envelope, after cross-talk is removed. In the latter case, candidate thresholds are selected on the bases of the signal data collected.

FIG. 4 illustrates an embodiment of a method 400 for detecting the first arrival of a signal that includes collecting signals from all selected paths (block 405) of a transducer array 110. Cross-talk is removed (block 200) from each signal, for example, in the manner described above, and the envelope of both the excitation signal and the remaining portion of the detected signal is computed (block 415). A set of thresholds of selected values are ordered sequentially and assigned an indexing number k, beginning with k=1, up to the maximum number of threshold values M (block 425). The kth value of threshold $TH^k$ is selected and applied (block 430) to the envelope obtained in block 415. The propagation time of the first arrival wave packet is computed as the time from the instant of the maximum of the excitation signal envelope to the instant of the first local maximum of the received signal envelope that exceeds the first candidate amplitude threshold. One may also use other methods such as cross-correlation between the two envelopes to calculate the propagation time of the first arrival wave packet. As this calculation has been performed for all paths, a group velocity may be computed (block 440) for each path by dividing the known path length by the propagation time of the first arrival wave packet.

A "cost function" may be defined as the variance of the signal group velocities computed for all paths in block 440, which may be computed and associated with the threshold $TH^k$, group velocity, and corresponding first arrival wave packet propagation time, all of which may be stored as an ordered set of values (block 445).

k may then be incremented and a test applied to determine if all values of $TH^k$ have yet been evaluated (decision block 450). A No result in decision block 450 returns the method to block 430 and the envelope is tested to find a new first arrival wave packet propagation time, and group velocity for each path subject to the new threshold condition (repeating blocks 430-445). When all threshold values $TH^k$ have been exhausted (a Yes result in decision block 450), the threshold with the lowest corresponding cost function is selected (block 455).

With the selected threshold, the true first arrival wave packet can be selected for each path (block 460). First, the propagation time of the first arrival wave packet that corresponds to the selected threshold is already computed. A local maximum of the received signal envelope, $Y_{max}$ can then be located at the time $t_{max}$ that is the propagation time plus the time of the maximum of the excitation signal envelope. As in the first embodiment, a threshold window of time width THwin is specified, on the basis of the time characteristics of the exciting signal applied to the transmitting sensor and the response of the transmitting sensor to that signal. The starting and ending time of the first arrival wave packet can then be determined. More specifically, let Y be the value of the envelope of the received signal at some time t. Starting from the local maximum $Y_{max}$ mentioned above, the value of Y is decreased gradually. Let t1 and t2 be the times where the envelope value equals Y and t1 and t2 are the closest time to $t_{max}$ from its right and left sides. Then, when t2−t1 equals THwin, the value of t1 and t2 are specified as the starting and ending time of the first arrival wave packet. The first arrival wave packet starting and ending time t1 and t2 corresponding to the lowest cost function are the result of the best selected threshold, and are provided as the resulting output (block 460).

It may be appreciated, for example, that if the threshold is chosen to have a low value, noise appearing early in many of the signal waveforms may produce an erroneously high calculated group velocity in the corresponding paths, with a consequent increase in variance, i.e., cost function value. On the other hand, if the threshold value is chosen too high, weaker signals from some paths may not be accepted, by virtue of failing to meet a threshold requirement for any portion of the signal in a relevant time window. In this case, a group velocity of substantially zero may be calculated, as no signal has been detected as arriving during any length of time. Choosing a threshold intermediate of these two extreme cases can result in few or no errors in detecting a signal first arrival. Within the limits of noise, signal amplitude variation, and resolution, the group velocities of all signal paths can be detected and will lie in a very narrow band of values. Thus, the cost function (i.e., variance) will be correspondingly much smaller than for other values of threshold.

Therefore, as described above, selecting a candidate threshold that is either too low or too high will result in a variance in the group velocity (i.e., the cost value) that is larger than a range in which the cost value is low, i.e., the group velocity can be reliably estimated over substantially all paths.

Figure 5:
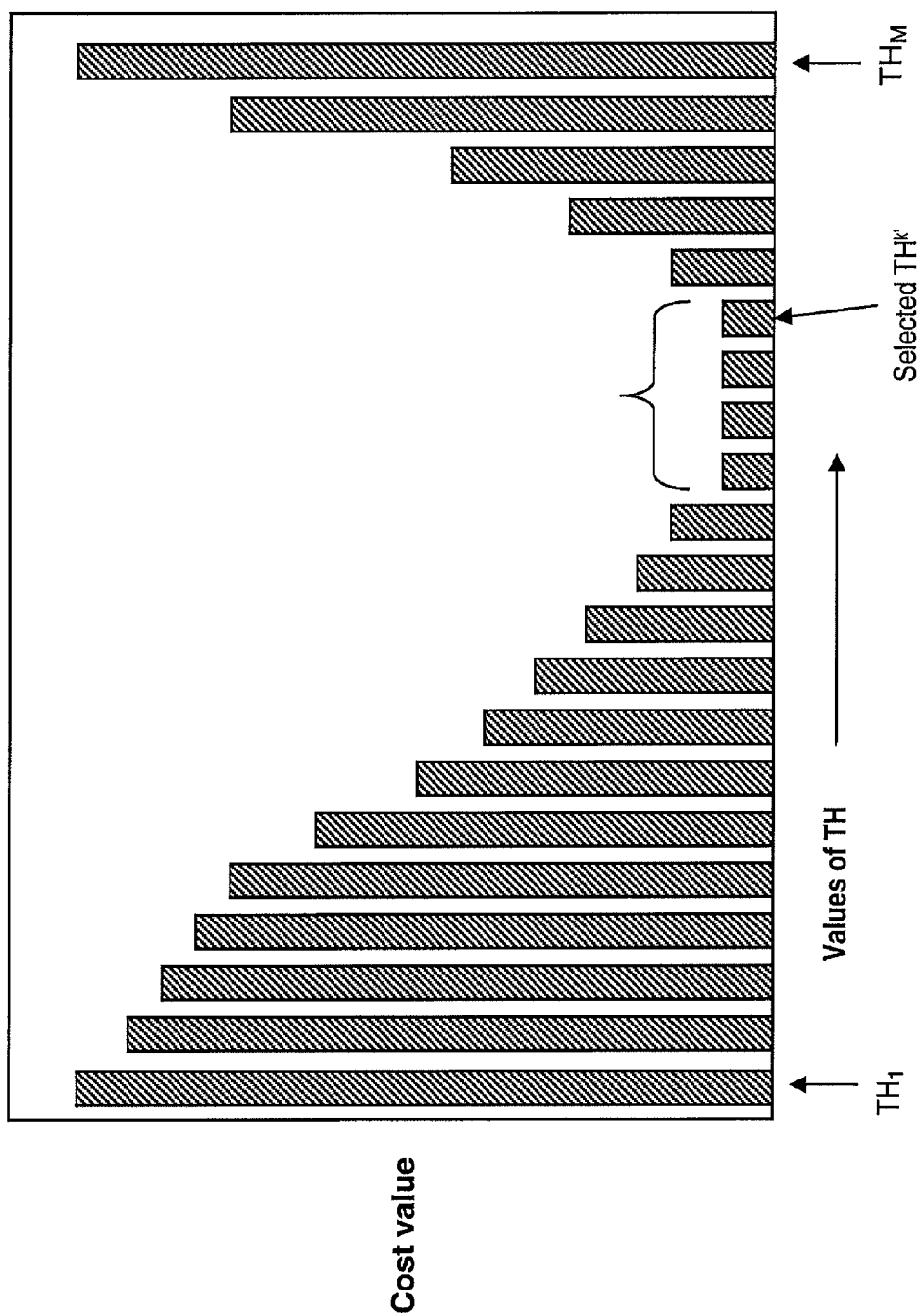
FIG. 5 shows an exemplary cost function dependence on threshold selection according to the method of FIG. 4.

FIG. 5 shows an exemplary cost function dependence on threshold selection. Ideally, the minimum cost value would occur for a single $TH^{k'}$. The next step of the process may be used to detect the first arrivals using the "optimal threshold." However, due to the granularity of the values of the candidate thresholds, there may be more than one "optimal" threshold value, i.e., several neighboring candidate thresholds may yield substantially the same cost value. Therefore, the largest threshold of all thresholds having substantially equal cost value may be selected as the detection threshold with no loss in reliability or accuracy of the method.

FIGS. 6 A-C show estimated group velocity calculations of the wave speed for every path in a test structure with 217 paths for different candidate thresholds. Candidate thresholds may be selected in various ways. In the particular exemplary cases illustrated in FIGS. 6 A-C, the signal may be digitized using, for example, a 12-bit analog-to-digital (AD) converter. Thus, the signal may be scaled and resolved in a range between −2047 and +2048 digital values. Candidate thresholds may be selected in this range, e.g., 20, 40, 60, 80, . . . , 160, and so on.

Figure 6A:
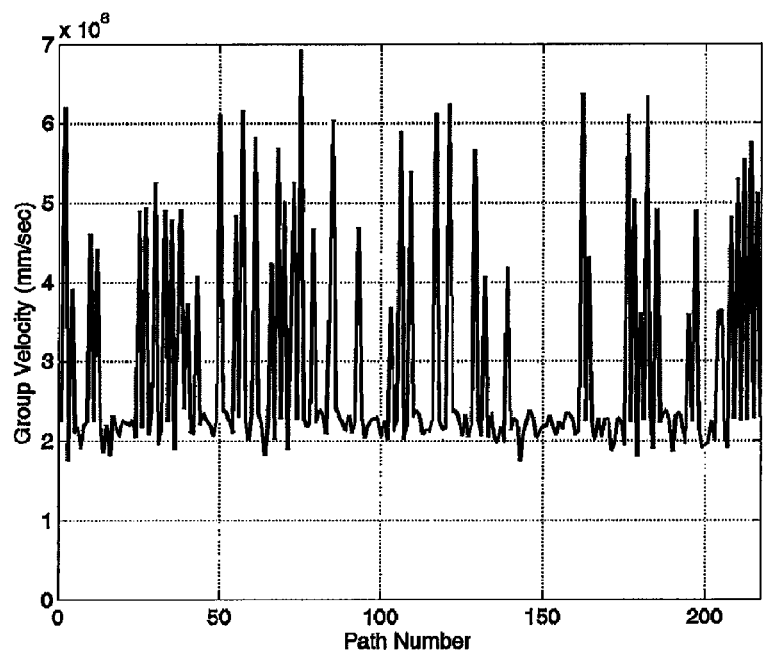
FIGS. 6A-6C show exemplary cases of group velocity estimation for candidate thresholds, according to an embodiment of the disclosure.

FIG. 6A corresponds to group velocity calculations when the candidate threshold selected is a relatively low value (e.g., 20). Using this candidate threshold, noise in the system may be prematurely and mistakenly taken as the minimum value of the first arrival, and will result in an unreliable calculation of group velocity. That is, for some paths, the estimated group velocity is so high as not to be physically meaningful for an elastic wave in the structural medium. This may result in a significantly large variance of the 217 calculated velocities, and a correspondingly higher velocity variance, or cost function value. Thus, high cost values are an indicator of unreliable threshold selection through unreliable velocity calculation results.

Figure 6B:
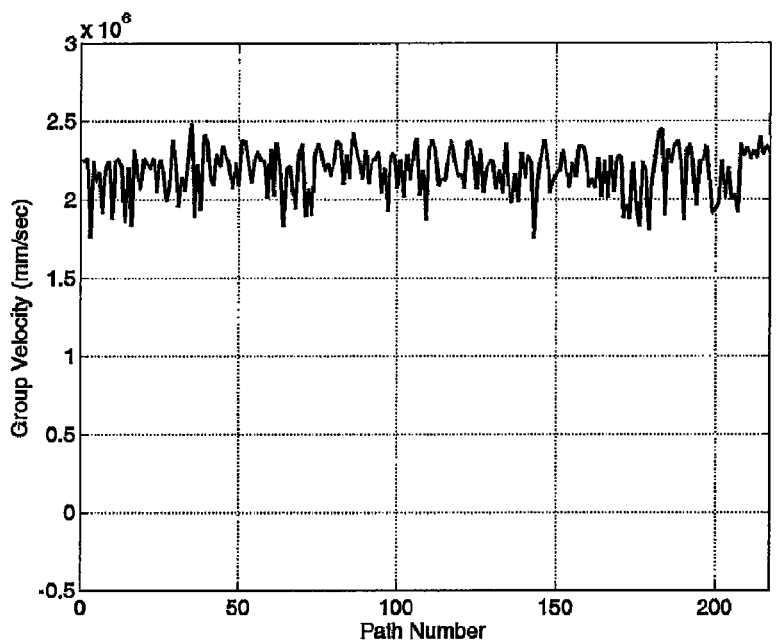

FIG. 6B illustrates the group velocity calculation when a threshold is chosen (e.g., 100) that results in a fairly stable and uniform calculation of group velocity for all paths. Thus, the variance is quite small, i.e., the cost function value is near a minimum, even if it is not ideal. An ideal cost value of zero corresponds in FIG. 6 at a flat line in FIG. 6 at a group velocity measured at precisely the same value for all paths.

Figure 6C:
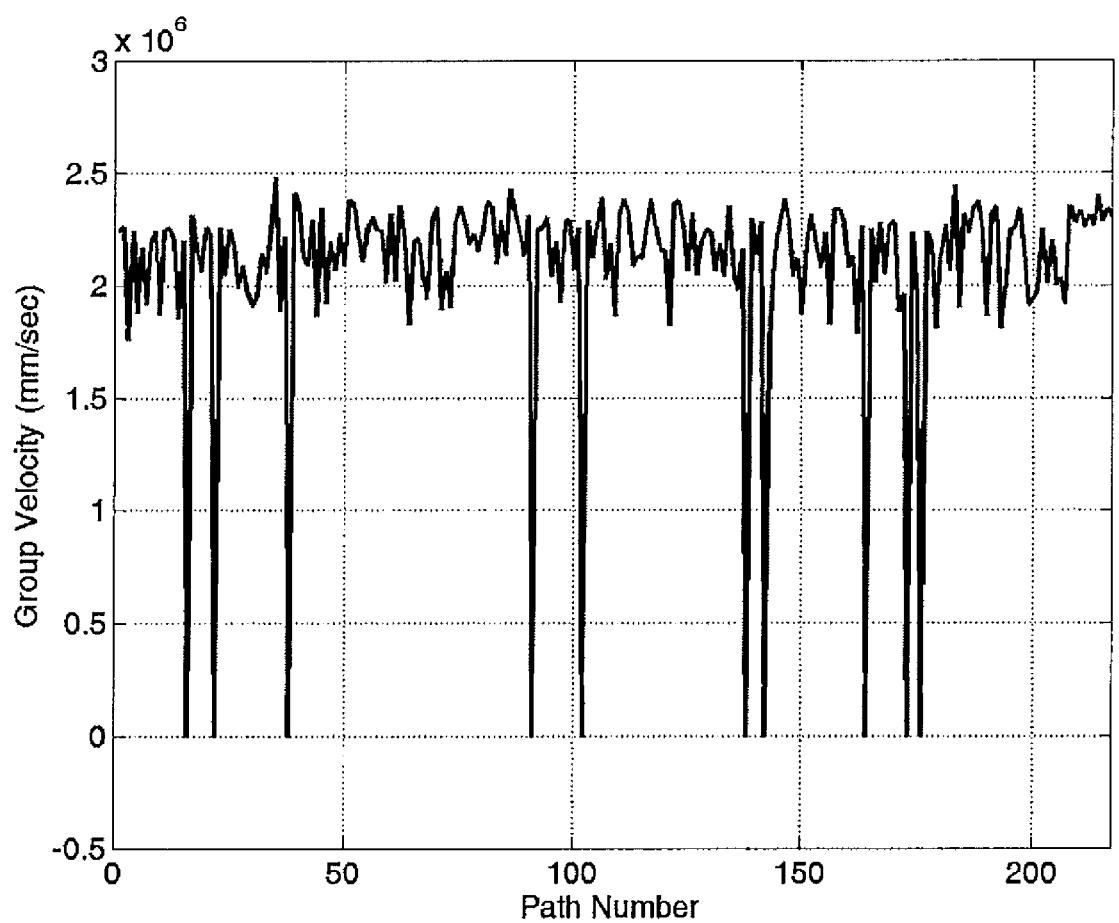

Selecting a threshold that is too high may result in signals on some paths not exceeding the threshold at any point in the relevant time window. Furthermore, a higher threshold will increase the time delay at which the signal envelope crosses the amplitude threshold level, which will result in a lower group velocity. FIG. 6C is an example of the group velocity calculations when too large a threshold (e.g., 300) is chosen. When the threshold is too high, some signals may not exceed the threshold at any point in the signal window, producing an effective velocity measurement of zero. As may be seen in FIG. 6C, a larger cost value (variance) in group velocity will result as compared to the cost value corresponding to the threshold value 100 of FIG. 6B discussed above, an indication that the threshold candidate value 300 results in a determination of group velocity that is less reliable than the former.

The granularity of the selection of candidate thresholds may be varied to suit various objectives. For example, a finer granularity may provide a smaller minimum cost value (velocity variance) and more accurate time of arrival, which comes at the cost of increased computation. A coarser granularity may provide a satisfactory cost value, i.e., within a selected range, and sufficient accuracy in determining the time of arrival, as determined by the cost value.

One can appreciate that this process may be executed based substantially on signal path data, and makes little or no assumption about details of the structure. If a structure is, for example, comprised of a graphite epoxy laminate material, or is subject to highly directional loads, the group velocity may vary with direction of the path. Lack of uniformity in transducers and transducer bonding may further contribute to a lack of absolute uniformity in the measurement of group velocity for all paths. Some systemic wander about the mean value of group velocity may be observed in the various group velocity graphs such as those of FIGS. 6A-6C due to anisotropy in the structural material. This, however, may be a slowly varying function of propagation direction, and may vary within a restricted range of values. By recognizing that a larger minimum value of the cost function is to be expected corresponding to the degree of velocity anisotropy, and which may increase the variance of group velocity, the effect of velocity direction anisotropy may be compensated for, based on propagation direction of the selected path.

Although the present disclosure has been described with reference to certain exemplary embodiments thereof, it will be understood by those skilled in the art that a variety of modifications and variations may be made thereto without departing from the spirit or scope of the present disclosure defined in the appended claims, and their functional equivalents.

What is claimed is:

1. A method for detecting the first arrival wave packet of an acoustic signal at a transducer of a structural health monitoring (SHM) system, the method comprising:

selecting a path between a pair of transducers of an array of transducers attached to the structure, each transducer being operable to generate and apply an acoustic signal to the structure in response to the application of an electrical excitation signal thereto, and to detect an acoustic signal in the structure and to generate and output an electrical signal corresponding to the acoustic signal detected;

transmitting an acoustic signal through the structure and along the selected path from a first one of the transducers;

receiving the signal transmitted from the first transducer with the second transducer;

removing electromagnetic cross-talk from the received signal; and, detecting the first arrival wave packet of the acoustic signal at the receiving transducer;

wherein the removing of the electromagnetic cross-talk comprises:

specifying an upper bound for a group velocity of an acoustic signal transmitted on the selected path between the first and second transducers;

computing a lower bound of a time of transmission along the selected path by dividing the distance of the selected path by the specified upper bound of the group velocity;

computing a gate time equal to the sum of the lower bound of the transmission time and a trigger time corresponding to the excitation of the signal at the first transducer; and retaining only the data in a signal waveform corresponding to times greater than the gate time.

2. A method for detecting the first arrival wave packet of an acoustic signal at a transducer of a structural health monitoring (SHM) system, the method comprising:

selecting a path between a pair of transducers of an array of transducers attached to the structure, each transducer being operable to generate and apply an acoustic signal to the structure in response to the application of an electrical excitation signal thereto, and to detect an acoustic signal in the structure and to generate and output an electrical signal corresponding to the acoustic signal detected;

transmitting an acoustic signal through the structure and along the selected path from a first one of the transducers;

receiving the signal transmitted from the first transducer with the second transducer;

removing electromagnetic cross-talk from the received signal; and, detecting the first arrival wave packet of the acoustic signal at the receiving transducer;

wherein the detecting of the first arrival wave packet comprises:

specifying an amplitude threshold;

specifying a time width threshold;

computing an envelope of the entire received excitation signal following the removal of the cross-talk from the signal;

determining the time location of all local maxima in the envelope of the signal;

selecting a first local maximum in the envelope with a signal amplitude greater than the specified amplitude threshold;

determining whether the envelope of the local maximum has a duration greater than the specified time width threshold;

setting the first arrival wave packet as the signal segment starting from the time at which the signal envelope exceeds the specified amplitude threshold and ending at the time that equals the starting time plus the time width threshold if the amplitude of the envelope has a duration greater than the specified time width threshold;

repeating the selecting a first local maximum, determining whether, and setting the first arrival wave packet for a next local maximum if the amplitude of the envelope corresponding to the previous local maximum does not exceed the specified amplitude threshold for the specified time width threshold until a signal portion corresponding to a local maximum in the signal is found that exceeds the specified amplitude and time width thresholds; and, deciding that no first arrival was detected in the signal if no portion of the signal envelope exceeds the amplitude threshold for the time width threshold specified.

3. The method of claim 2, further comprising repeating the detecting of the first arrival time for all paths in the array.

4. A method for detecting the first arrival wave packet of an acoustic signal at a transducer of a structural health monitoring (SHM) system, the method comprising:

selecting a path between a pair of transducers of an array of transducers attached to the structure, each transducer being operable to generate and apply an acoustic signal to the structure in response to the application of an electrical excitation signal thereto, and to detect an acoustic signal in the structure and to generate and output an electrical signal corresponding to the acoustic signal detected;

transmitting an acoustic signal through the structure and along the selected path from a first one of the transducers;

receiving the signal transmitted from the first transducer with the second transducer;

removing electromagnetic cross-talk from the received signal; and, detecting the first arrival wave packet of the acoustic signal at the receiving transducer;

wherein the detecting of the first arrival wave packet comprises:

(A) selecting a set of candidate threshold values based on the range of the amplitude of the detected signals, wherein a counter number is assigned to each candidate in an ascending order corresponding to an increase in the value of the candidate threshold;

(B) computing an envelope of the excitation signal applied to the transmitting transducers and an envelope of each of the entire detected signals following the removal of the cross-talks from the signals;

(C) selecting a candidate threshold;

(D) applying the candidate threshold to the envelope of a detected signal;

(E) setting the propagation time of the first arrival wave packet as the time from the instant of the maximum of the excitation signal envelope to the instant of the first local maximum of the received signal envelope that exceeds the candidate amplitude threshold;

(F) determining the group velocity for the path on the basis of the propagation time of the first arrival wave packet and the known distance;

(G) repeating (D)-(F) for all selected paths between all pairs of transducers in the array;

(H) calculating a cost value corresponding to the candidate threshold value and counter number, wherein the cost value is a variance of the group velocities of all the selected paths corresponding to the candidate threshold;

(I) repeating (C)-(H) for each candidate threshold until all thresholds have been applied;

(J) selecting the threshold corresponding to the smallest cost value obtained; and, (K) selecting the wave packet first arrival time on the basis of the threshold corresponding to the smallest cost value.

5. The method of claim 4, wherein the selecting of the set of candidate threshold values is determined on the basis of the minimum and maximum values of the envelopes of the received signals.

6. The method of claim 4, wherein the selecting of the set of candidate threshold values is a fixed set of values in a selected range of values.

* * * * *